(12) United States Patent
Sada et al.

(10) Patent No.: US 6,878,703 B2
(45) Date of Patent: Apr. 12, 2005

(54) PHARMACEUTICAL COMPOSITION

(75) Inventors: Toshio Sada, Tokyo (JP); Makoto Mizuno, Funabashi (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/442,874

(22) Filed: May 20, 2003

(65) Prior Publication Data

US 2004/0002529 A1 Jan. 1, 2004

Related U.S. Application Data

(63) Continuation of application No. PCT/JP01/10095, filed on Nov. 19, 2001.

(30) Foreign Application Priority Data

| Nov. 21, 2000 | (JP) | 2000-354327 |
| May 31, 2001 | (JP) | 2001-164009 |

(51) Int. Cl.[7] ............... A61K 31/54; A61K 31/41
(52) U.S. Cl. ................. 514/223.5; 514/381
(58) Field of Search ............... 514/223.5, 382, 514/381

(56) References Cited

U.S. PATENT DOCUMENTS

| 2,554,816 A | 5/1951 | Clapp et al. |
| 2,783,241 A | 2/1957 | Young et al. |
| 2,835,702 A | 5/1958 | Schultz |
| 2,976,289 A | 3/1961 | Cohen et al. |
| 2,980,679 A | 4/1961 | Pala |
| 3,009,911 A | 11/1961 | McManus |
| 3,025,292 A | 3/1962 | Jones et al. |
| 3,055,904 A | 9/1962 | Graf et al. |
| 3,058,882 A | 10/1962 | Stürm et al. |
| 3,108,097 A | 10/1963 | Ugi |
| 3,163,645 A | 12/1964 | de Stevens et al. |
| 3,183,243 A | 5/1965 | Lee et al. |
| 3,254,076 A | 5/1966 | Lund et al. |
| 3,255,241 A | 6/1966 | Schultz et al. |
| 3,265,573 A | 8/1966 | Goldberg |
| 3,313,813 A | 4/1967 | Cragoe, Jr. |
| 3,356,692 A | 12/1967 | Horstmann et al. |
| 3,360,518 A | 12/1967 | Shetty |
| 3,567,777 A | 3/1971 | Liebenow |
| 3,634,583 A | 1/1972 | Feit |
| 3,758,506 A | 9/1973 | Godfroid et al. |
| 5,138,069 A | 8/1992 | Carini et al. |
| 5,153,197 A | 10/1992 | Carini et al. |
| 5,264,447 A | * 11/1993 | Ohtawa ............... 514/381 |
| 5,310,928 A | 5/1994 | Lo et al. |
| 5,616,599 A | * 4/1997 | Yanagisawa et al. ....... 514/381 |
| 5,656,650 A | * 8/1997 | Weinstock ............... 514/396 |

FOREIGN PATENT DOCUMENTS

| BE | 639386 | 10/1963 |
| EP | 0 400 835 A1 | 12/1990 |
| EP | 0 503 785 A1 | 9/1992 |
| EP | 0 733 366 A2 | 9/1996 |
| GB | 795174 | 5/1958 |
| GB | 851287 | 10/1960 |
| WO | WO 89/06233 A1 | 7/1989 |

OTHER PUBLICATIONS

Krousel–Wood et al., "Primary Prevention of Essential Hypertension", Med. Clncs. of North Am., (Jan. 2004) 88(1) 223–38. (Abstract only).*

C.W. Whitehead et al., Diuretics, V, 3,4–Dihydro–1,2, 4–benzothiadiazine 1,1–Dioxides, *J. Org. Chem.*, 26, (1961), pp. 2814–2818.

Stevens et al., *Experientia*, "The Chemistry and Pharmacology of Hydrotrichlorothiazide", 16, (1960), p. 113–114.

Close et al., "Synthesis of Potential Diuretic Agents. I. Derivatives of 7–Sulfamyl–3,4–dihydro–1,2,4–benzothiadiazine 1,1–Dioxide", *J. Am. Chem. Soc.*, 82, (1960), pp. 1132–1135.

Jucker et al., "Über diuretisch wirksame Benzoesäure–Derivate", *Helv. Chim. Acta.*, 45, (1962), pp. 2316–2325.

(Continued)

Primary Examiner—Raymond J. Henley, III
(74) Attorney, Agent, or Firm—Frishauf, Holtz, Goodman & Chick, P.C.

(57) ABSTRACT

A pharmaceutical composition comprises an angiotensin II receptor antagonist selected from among compounds having the following formula (I), a pharmacologically acceptable salt thereof, a pharmacologically acceptable ester thereof and a pharmacologically acceptable salt of such ester, and one or more diuretics:

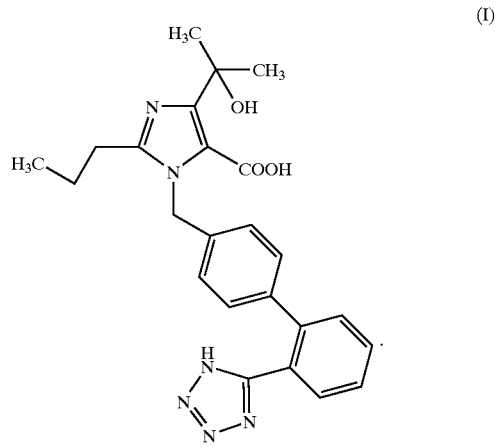

(I)

The pharmaceutical composition of the present invention has an excellent hypotensive effect and low toxicity, and therefore is useful as a medicament for preventing or treating hypertension or heart disease.

15 Claims, No Drawings

OTHER PUBLICATIONS

Satoh et al., "Enhancement of the Hypotensive Effect of Hydralazine by a New Sulfamoylbenzamide Type Diuretic–hypotensive Agentin DOCA–hypertensive Rats", *Oyo Yakuri, 21* (1981), pp. 607–611.

Davies et al., "The Comparative Effects of the Nitro–, Carboxyl, and Sulphonic Acid Groups on the Hydrolysis of Aryl Halides", *J. Chem. Soc.,* (1928), pp. 1122–1131.

E. Jucker and A. Lindenmann, "Diuretic Activities of Benzoic Acid Derivatives", *Helv. Chim. Acta.,* 45 (1962), pp. 2316–2325.

Graul, A. et al., "CS–866: Antihypertensive Angiotensin II Antagonist", *Drugs of the Future,* vol. 22, No. 11, Nov. 1997, pp. 1205–1209.

Danser, A.J. et al. "18th Scientific Meeting of the International Society of Hypertension", *Expert Opinion on Investigational Drugs,* Ashley Publications Ltd., London, GB, vol. 9, No. 10, Aug. 20, 2000, pp. 2419–2423.

Critchley, Julian A.J.H. et al., "A Randomized, Double–Masked Comparison of the Antihypertensive Efficacy and Safety of Combination Therapy with Losartan and Hydrochlorothiazide Versus Captopril and Hydrochlorothiazide in Elderly and Younger Patients", *Current Therapeutic Research,* vol. 57, No. 5, 1996, pp. 392–407.

Koike, H., et al., "In vitro and In vivo pharmacology of olmesartan medoxomil, an angiotensin II type $AT_1$ receptor antagonist", *Journal of Hypertension,* vol. 19 (Suppl. 1) pp. S3–S14, Jun. 2001.

Brunner, Hans R., "Olmesartan medoxomil: a new $AT_1$ receptor antagonist for the treatment of hypertension", *Journal of Hypertension,* vol. 19 ((Suppl. 1) S1–S2, Jun. 2001.

Brunner, Hans R., "Relevance of clinical pharmacological models for the evaluation of threapeutic dose range of an $AT_1$–receptor antagonist", *Journal of Hypertension,* vol. 19 (Suppl. 1) S15–S20, Jun. 2001.

Laeis, Petra, et al., "The pharmacokinetic and metabolic profile of olmesartan medoxomil limits the risk of clinically relevant drug interaction", *Journal of Hypertension,* vol. 19 (Suppl. 1) S21–S48, Jun. 2001.

Von Bergmann, Klaus, et al., "Olmesartan moedoxomil: influence of age, renal and hepatic function on the pharmacokinetics of olmesartan medoxomil", *Journal of Hypertension,* vol. 19 (Suppl. 1), S33–S40, Jun. 2001.

Püchler, Kurt, et al., "Blood pressure response, but not adverse event incidence, correlates with dose of angiotensin II antagonist", *Journal of Hypertension,* vol. 19 (Suppl. 1), S41–S48, Jun. 2001.

Fliser, Danilo, et al., "Angiotensin II subtype 1–receptor antagonists in the treatment of diabetic nephropathy", *Journal of Hypertension,* vol. 19 (Suppl. 1) S57–S60, Jun. 2001.

McInnes, Gordon T., "Clinical potential: angiotensin converting enzyme inhibitor or angiotensin II antageonist?", *Journal of Hypertension,* vol. 19 (Suppl. 1) S61–S67, Jun. 2001.

Ball, Keith J., "Relative efficacy of an angiotensin II antagonist compared with other antihypertensive agents. Olmesartan medoxomil versus antihypertensives", *Journal of Hypertension,* vol. 19 (Suppl. 1) S49–S56, Jun. 2001.

* cited by examiner

PHARMACEUTICAL COMPOSITION

CROSS-REFERENCE TO RELATED APPLICATION

This application is a Continuation application of International application No. PCT/JP01/10095, filed Nov. 19, 2001, the entire contents of which are hereby incorporated by reference herein.

BACKGROUND OF THE INVENTION

1. Field of the Invention

The present invention relates to a pharmaceutical composition containing a specific angiotensin II receptor antagonist and one or more diuretics as the active ingredients (particularly a pharmaceutical composition for preventing or treating hypertension), the use of a specific angiotensin II receptor antagonist and one or more diuretics for manufacturing the pharmaceutical composition (particularly a pharmaceutical composition for preventing or treating hypertension), and a method for preventing or treating (particularly treating) diseases (particularly hypertension) by the administration of a pharmaceutical composition to warm-blooded animals (particularly humans) comprising effective doses of a specific angiotensin II receptor antagonist and one or more diuretics.

2. Background Information

It is known that co-administration of an angiotensin II receptor antagonist and a diuretic is an effective therapy for the prevention or treatment of hypertension (particularly treatment). These pharmaceutical compositions are described, for example, in WO89/6233, Japanese Patent Application Kokai No. Hei 3-27362 and the like.

However, the effects of a pharmaceutical composition containing a specific angiotensin II receptor antagonist, such as CS-866 ((5-methyl-2-oxo-1,3-dioxolen-4-yl)methyl 4-(1-hydroxy-1-methylethyl)-2-propyl-1-[2'-(1H-tetrazol-5-yl)biphenyl-4-ylmethyl]imidazol-5-carboxylate) (U.S. Pat. No. 5,616,599)), and a diuretic remain unknown.

SUMMARY OF THE INVENTION

Considering that prevention and/or treatment of hypertension are important, the present inventors investigated combinations of various drugs and found that a pharmaceutical composition containing a specific angiotensin II receptor antagonist, such as CS-866, and one or more diuretics exerts excellent anti-hypertensive effects and hence may be useful as a preventative and/or therapeutic agent for hypertension.

The present invention provides a pharmaceutical composition containing a specific angiotensin II receptor antagonist and one or more diuretics as the active ingredients (particularly pharmaceutical compositions for preventing or treating hypertension), the use of a specific angiotensin II receptor antagonist and one or more diuretics for manufacturing the pharmaceutical compositions (particularly pharmaceutical compositions for preventing or treating hypertension), a method for preventing or treating (particularly treating) diseases (particularly hypertension) by the administration of a specific angiotensin II receptor antagonist and one or more diuretics to warm-blooded animals (particularly humans) at effective doses, and a pharmaceutical composition for administering simultaneously or sequentially a specific angiotensin II receptor antagonist and one or more diuretics for preventing or treating hypertension.

DETAILED DESCRIPTION OF THE INVENTION

The active ingredients of the pharmaceutical composition of this invention include an angiotensin II receptor antagonist selected from the group consisting of a compound having the following formula (I), pharmacologically acceptable salts thereof, pharmacologically acceptable esters thereof and pharmacologically acceptable salts of said esters; and one or more diuretics.

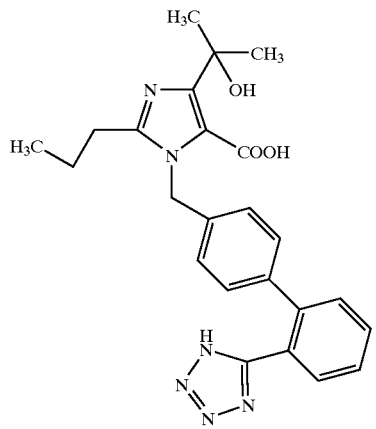

(I)

The compound of formula (I), a salt thereof and the like are known compounds, for example, described in the specification of Japanese Patent Application Kokai No. Hei 5-78328 etc. and the chemical name of the compound of formula (I) is 4-(1-hydroxy-1-methylethyl)-2-propyl-1-[2'-(1H-tetrazol-5-yl)biphenyl-4-ylmethyl]imidazol-5-carboxylic acid.

The "pharmacologically acceptable salt" of the compound of formula (I), which is an active ingredient of this invention, includes an alkali metal salt such as sodium salt, potassium salt or lithium salt; an alkaline earth metal salt such as calcium salt or magnesium salt; a metal salt such as aluminum salt, iron salt, zinc salt, copper salt, nickel salt or cobalt salt; or an amine salt such as ammonium salt, t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt or tris(hydroxymethyl)aminomethane salt. An alkali metal salt is preferable and the sodium salt is particularly preferable.

The "pharmacologically acceptable ester" of the compound of formula (I), which is an active ingredient of this invention, is a compound esterified at the carboxyl moiety of the compound of formula (I). A group forming said ester is a group which can be cleaved by a biological process such as hydrolysis in vivo. Such groups include, for example, a $(C_1-C_4)$alkoxy-$(C_1-C_4)$alkyl group such as methoxymethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, propoxymethyl, isopropoxymethyl, butoxymethyl or t-butoxymethyl; a $(C_1-C_4)$alkoxylated $(C_1-C_4)$alkoxy-$(C_1-C_4)$alkyl group such as 2-methoxyethoxymethyl; a $(C_6-C_{10})$aryloxy-$(C_1-C_4)$alkyl group such as phenoxymethyl; a halogenated $(C_1-C_4)$alkoxy-$(C_1-C_4)$alkyl group such as 2,2,2- trichloroethoxymethyl or bis(2-chloroethoxy)methyl; a ($C_1$–$C_4$)alkoxycarbonyl-($C_1$–$C_4$)alkyl group such as methoxycarbonylmethyl; a cyano-($C_1$–$C_4$)alkyl group such as cyanomethyl or 2-cyanoethyl; a ($C_1$–$C_4$)alkylthiomethyl group such as methylthiomethyl or ethylthiomethyl; a ($C_6$–$C_{10}$)arylthiomethyl such as phenylthiomethyl or naphthylthiomethyl; a ($C_1$–$C_4$)alkylsulfonyl-($C_1$–$C_4$) lower alkyl group, which may be optionally substituted with a halogen atom(s), such as 2-methanesulfonylethyl or 2-trifluoromethanesulfonylethyl; a ($C_6$–$C_{10}$)arylsulfonyl-($C_1$–$C_4$)alkyl group such as 2-benzenesulfonylethyl or 2-toluenesulfonylethyl; an aliphatic ($C_1$–$C_7$)acyloxy-($C_1$–$C_4$)alkyl group such as formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl, or 1-pivaloyloxyhexyl; a ($C_5$–$C_6$)cycloalkylcarbonyloxy-($C_1$–$C_4$)alkyl group such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl; a ($C_6$–$C_{10}$)arylcarbonyloxy-($C_1$$C_4$)alkyl group such as benzoyloxymethyl; a ($C_1$–$C_6$)alkoxycarbonyloxy-($C_1$–$C_4$)alkyl group such as methoxycarbonyloxymethyl, 1-(methoxycarbonyloxy)ethyl, 1-(methoxycarbonyloxy)propyl, 1-(methoxycarbonyloxy)butyl, 1-(methoxycarbonyloxy)pentyl, 1-(methoxycarbonyloxy)hexyl, ethoxycarbonyloxymethyl, 1-(ethoxycarbonyloxy)ethyl, 1-(ethoxycarbonyloxy)propyl, 1-(ethoxycarbonyloxy)butyl, 1-(ethoxycarbonyloxy)pentyl, 1-(ethoxycarbonyloxy)hexyl, propoxycarbonyloxymethyl, 1-(propoxycarbonyloxy)ethyl, 1-(propoxycarbonyloxy)propyl, 1-(propoxycarbonyloxy)butyl, isopropoxycarbonyloxymethyl, 1-(isopropoxycarbonyloxy)ethyl, 1-(isopropoxycarbonyloxy)butyl, butoxycarbonyloxymethyl, 1-(butoxycarbonyloxy)ethyl, 1-(butoxycarbonyloxy)propyl, 1-(butoxycarbonyloxy)butyl, isobutoxycarbonyloxymethyl, 1-(isobutoxycarbonyloxy)ethyl, 1-(isobutoxycarbonyloxy)propyl, 1-(isobutoxycarbonyloxy)butyl, t-butoxycarbonyloxymethyl, 1-(t-butoxycarbonyloxy)ethyl, pentyloxycarbonyloxymethyl, 1-(pentyloxycarbonyloxy)ethyl, 1-(pentyloxycarbonyloxy)propyl, hexyloxycarbonyloxymethyl, 1-(hexyloxycarbonyloxy)ethyl or 1-(hexyloxycarbonyloxy)propyl; a ($C_5$–$C_6$)cycloalkyloxycarbonyloxy-($C_1$–$C_4$)alkyl group such as cyclopentyloxycarbonyloxymethyl, 1-(cyclopentyloxycarbonyloxy)ethyl, 1-(cyclopentyloxycarbonyloxy)propyl, 1-(cyclopentyloxycarbonyloxy)butyl, cyclohexyloxycarbonyloxymethyl, 1-(cyclohexyloxycarbonyloxy)ethyl, 1-(cyclohexyloxycarbonyloxy)propyl, or 1-(cyclohexyloxycarbonyloxy)butyl; a [5-($C_1$–$C_4$)alkyl-2-oxo-1,3-dioxolen-4-yl]methyl group such as (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, (5-butyl-2-oxo-1,3-dioxolen-4-yl)methyl; [5-(phenyl, which may be optionally substituted with a ($C_1$–$C_4$)alkyl, ($C_1$–$C_4$)alkoxy group(s) or halogen atom(s))-2-oxo-1,3-dioxolen-4-yl] methyl group such as (5-phenyl-2-oxo-1,3-dioxolen-4-yl) methyl, [5-(4-methylphenyl)-2-oxo-1,3-dioxolen-4-yl] methyl, [5-(4-methoxyphenyl)-2-oxo-1,3-dioxolen-4-yl] methyl, [5-(4-fluorophenyl)-2-oxo-1,3-dioxolen-4-yl] methyl, [5-(4-chlorophenyl)-2-oxo-1,3-dioxolen-4-yl] methyl; or a phthalidyl group, which may be optionally substituted with a ($C_1$–$C_4$)alkyl or ($C_1$–$C_4$)alkoxy group(s), such as phthalidyl, dimethylphthalidyl or dimethoxyphthalidyl. Preferred ester groups are a pivaloyloxymethyl group, phthalidyl group or (5-methyl-2-oxo-1,3-dioxolen-4-yl) methyl group and the more preferred ester group is a (5-methyl-2-oxo-1,3-dioxolen-4-yl)methyl group.

The "pharmacologically acceptable salt of the pharmacologically acceptable ester" of the compound of formula (I), which is an active ingredient of this invention, includes a pharmacologically acceptable salt of the "pharmacologically acceptable ester" described above, for example, a hydrohalogenic acid salt such as hydrofluoride, hydrochloride, hydrobromide or hydroiodide; nitrate; perchlorate; sulfate; phosphate; a $C_1$–$C_4$ alkanesulfonic acid salt, which may be optionally substituted with a halogen atom(s) such as methanesulfonate, trifluoromethanesulfonate or ethanesulfonate; a $C_6$–$C_{10}$ arylsulfonic acid salt, which may be optionally substituted with a $C_1$–$C_4$ alkyl group(s), such as benzenesulfonate or p-toluenesulfonate; a $C_1$–$C_6$ aliphatic acid salt such as acetate, malate, fumarate, succinate, citrate, tartrate, oxalate or maleate; or an amino acid salt such as a glycine salt, lysine salt, alginine salt, ornitine salt, glutamic acid salt or aspartic acid salt. Preferred salts are hydrochloride, nitrate, sulfate or phosphate and the particularly preferred salt is hydrochloride.

The angiotensin II receptor antagonist, which is an active ingredient of this invention, is preferably the compound of formula (I) or a pharmacologically acceptable ester thereof, more preferably a pharmacologically acceptable ester of the compound of formula (I), and still more preferably the pivaloyloxymethyl, phthalidyl or (5-methyl-2-oxo-1,3-dioxolen-4-yl)methyl ester of compound of formula (I). The most preferred compound is (5-methyl-2-oxo-1,3-dioxolen-4-yl)methyl 4-(1-hydroxy-1-methylethyl)-2-propyl-1-[2'-(1H-tetrazol-5-yl)biphenyl-4-ylmethyl]imidazol-5-carboxylate (CS-866).

The compound of formula (I), which is an active ingredient of this invention, may absorb water or an organic solvent to form a hydrate or a solvate and the present invention encompasses such hydrates and solvates.

The diuretics, which are another active ingredient of this invention, are known compounds and, for example, include sulfonamide compounds such as acetazolamide, methazolamide, ethoxzolamide, clofenamide, dichlorphenamide, disulfamide, mefruside, chlorthalidone, quinethazone, furosemide, clopamide, tripamide, indapamide, chlorexolone, metolazone, xipamide, bumetanide, piretanide and X-54; thiazide compounds such as hydrochlorothiazide, methylclothiazide, benzylhydrochlorothiazide, trichloromethiazide, cyclopenthiazide, polythiazide, ethiazide, cyclothiazide, bendroflumethiazide, and hydroflumethiazide; phenoxyacetic acid compounds such as ethacrynic acid, tienilic acid, indacrinone and quincarbate; triamterene; amiloride; spironolactone; potassium canrenoate; torasemide; MK-447; and traxanox sodium which have been disclosed in U.S. Pat. No. 2,554,816, U.S. Pat. No. 2,980,679, U.S. Pat. No. 2,783,241, GB 795,174, *J. Chem. Soc.*, 1125 (1928), U.S. Pat. No. 2,835,702, GB 851,287, U.S. Pat. No. 3,356,692, U.S. Pat. No. 3,055,904, U.S. Pat. No. 2,976,289, U.S. Pat. No. 3,058,882, *Helv. Chim. Acta,* 45, 2316 (1962), *Pharmacometrics,* 21, 607 (1982), U.S. Pat. No. 3,183,243, U.S. Pat. No. 3,360,518, U.S. Pat. No. 3,567,777, U.S. Pat. No. 3,634,583, U.S. Pat. No. 3,025,292, *J. Am. Chem. Soc.,* 82, 1132 (1960), U.S. Pat. No. 3,108,097, *Experientia,* 16, 113 (1960), *J. Org. Chem.,* 26, 2814 (1961), U.S. Pat. No. 3,009,911, U.S. Pat. No. 3,265,573, U.S. Pat. No. 3,254,076, U.S. Pat. No. 3,255,241, U.S. Pat. No. 3,758,506, BE 639,386 and U.S. Pat. No. 3,163,645. The preferred diuretic is a thiazide compound and the more preferred one is hydrochlorothiazide.

The planar chemical formulae of typical diuretics are shown below:

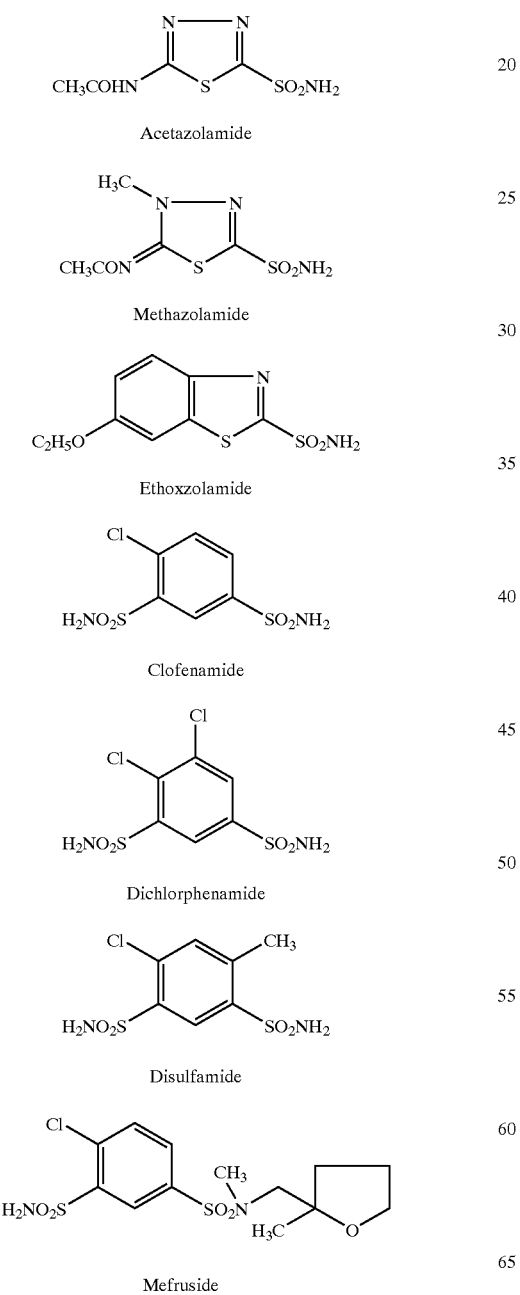

Acetazolamide

Methazolamide

Ethoxzolamide

Clofenamide

Dichlorphenamide

Disulfamide

Mefruside

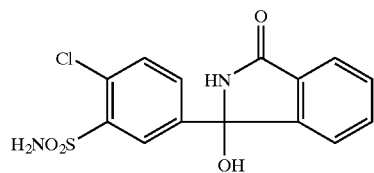

Chlorthalidone

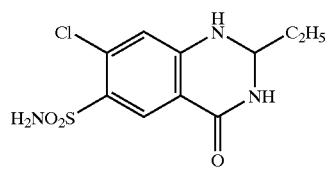

Quinethazone

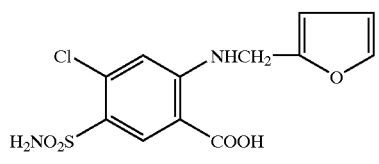

Furosemide

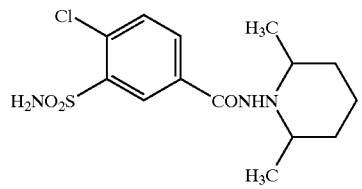

Clopamide

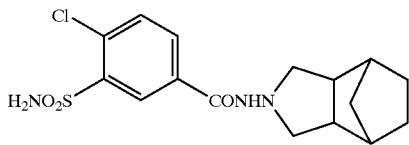

Tripamide

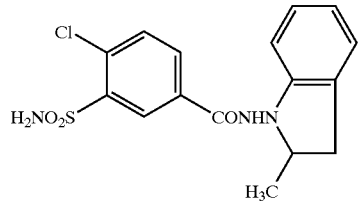

Indapamide

Clorexolone

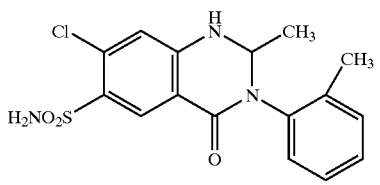
Metolazone
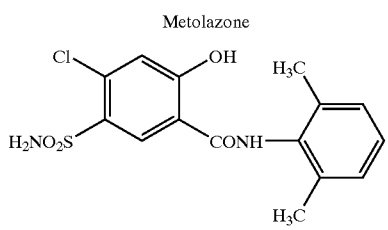
Xipamide
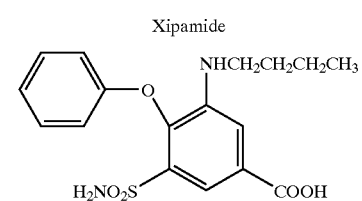
Bumetanide
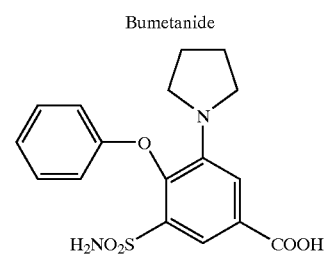
Piretanide
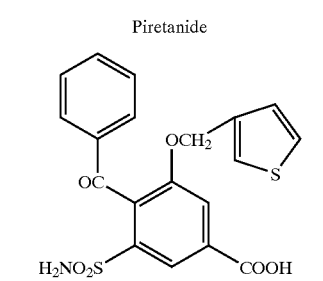
X-54
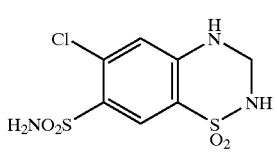
Hydrochlorothiazide
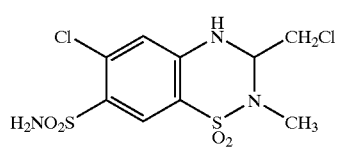
Methylclothiazide
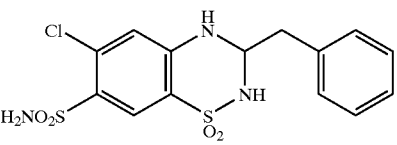
Benzylhydrochlorothiazide
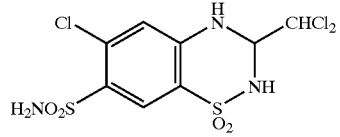
Trichloromethiazide
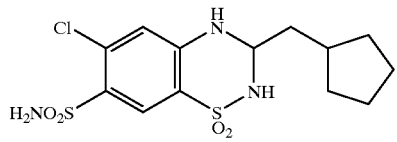
Cyclopenthiazide
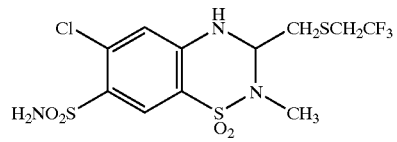
Polythiazide
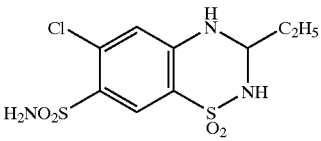
Ethiazide
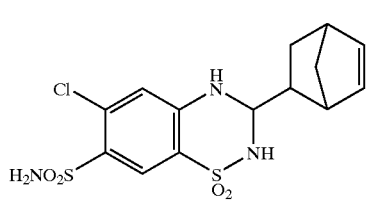
Cyclothiazide
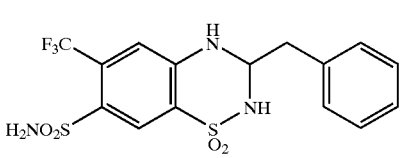
Bendroflumethiazide
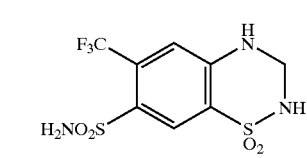
Hydroflumethiazide

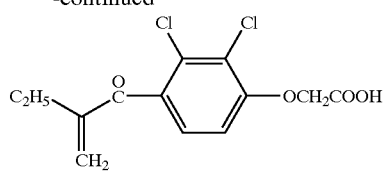

Ethacrynic acid

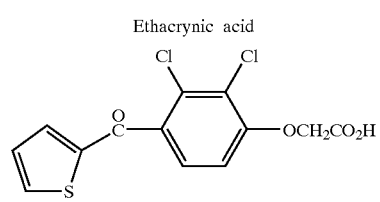

Tienilic acid

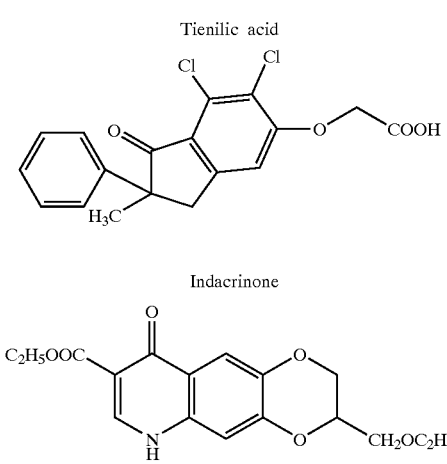

Indacrinone

Quincarbate

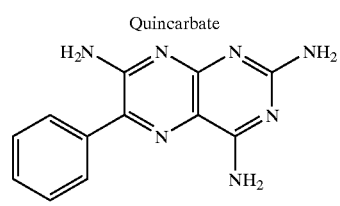

Triamterene

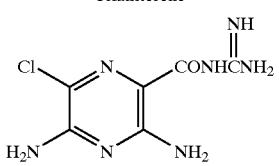

Amiloride

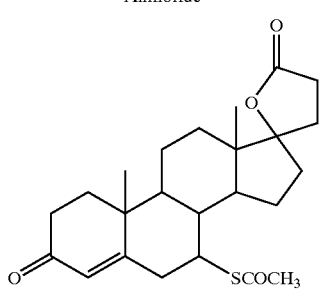

Spironolactone

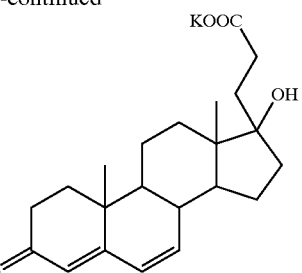

Potassium canrenoate

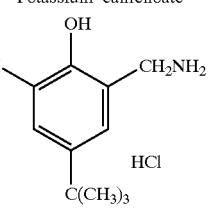

MK-447

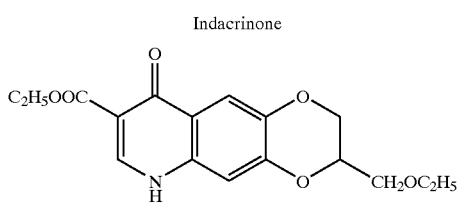

Torasemide

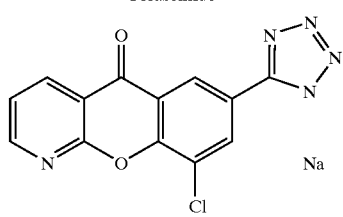

Traxanox sodium

The compound name of hydrochlorothiazide is 6-chloro-3,4-dihydro-2H-1,2,4,-benzothiadiazin-7-sulfonamide 1,1-dioxide. The hydrochlorothiazide of this invention includes pharmacologically acceptable salts thereof, for example, a hydrohalogenic acid salt such as hydrofluoride, hydrochloride, hydrobromide or hydroiodide; nitrate; perchlorate; sulfate; phosphate; a $C_1$–$C_4$ alkanesulfonic acid salt, which may be optionally substituted with a halogen atom(s) such as methanesulfonate, trifluoromethanesulfonate or ethanesulfonate; a $C_6$–$C_{10}$ arylsulfonic acid salt, which may be optionally substituted with a $C_1$–$C_4$ alkyl group(s), such as benzenesulfonate or p-toluenesulfonate; a $C_1$–$C_6$ aliphatic acid salt such as acetate, malate, fumarate, succinate, citrate, tartrate, oxalate or maleate; or an amino acid salt such as the glycine salt, lysine salt, alginine salt, ornitine salt, glutamic acid salt or aspartic acid salt. The preferred salts are the hydrochloride, nitrate, sulfate or phosphate and the particularly preferred salt is hydrochloride.

When the diuretic described hereinbefore has an asymmetric carbon(s), the present invention encompasses individual optical isomers and mixtures thereof. The present invention also encompasses hydrates of the compound described hereinbefore.

The diuretic of this invention is selected from one or more compounds described hereinbefore and preferably one diuretic agent is selected, which is used in combination with an angiotensin II receptor antagonist such as CS-866.

Preferred pharmaceutical compositions of this invention are:

(1) a pharmaceutical composition wherein the diuretic is a sulfonamide compound, a phenoxyacetic acid compound or a thiazide compound;

(2) a pharmaceutical composition wherein the diuretic is a thiazide compound;

(3) a pharmaceutical composition wherein the diuretic is selected from the group consisting of hydrochlorothiazide, methylclothiazide, benzylhydrochlorothiazide, trichloromethiazide, cyclopenthiazide, polythiazide, ethiazide, cyclothiazide, bendroflumethiazide and hydroflumethiazide; or (4) a pharmaceutical composition wherein the diuretic is hydrochlorothiazide.

Since the present invention, i.e., pharmaceutical compositions containing a specific angiotensin II receptor antagonist, such as CS-866, and one or more diuretics, exerts excellent antihypertensive actions and has low toxicities, the pharmaceutical compositions are useful as remedies, i.e., preferably preventative or therapeutic agents for hypertension, heart diseases (angina pectoris, cardiac failure, cardiac hypertrophy), vascular disorders (arteriosclerosis, post-PTCA restenosis, peripheral vascular disorders), renal diseases (diabetic nephropathy, glomerular nephritis, nephrosclerosis); more preferably preventative and/or therapeutic agents (particularly therapeutic agents) for hypertension or heart diseases; and most preferably preventative or therapeutic agents (particularly therapeutic agents) for hypertension]. The remedies described above are preferably applied to warm-blooded animals, especially to humans.

According to the present invention, the specific angiotensin II receptor antagonist such as CS-866 and diuretics exert better therapeutic efficacy by combined administration rather than when used separately. In addition, these agents exert excellent efficacy when administered to the same warm-blooded animal at different times. It is speculated that when the 2 groups of compounds employed in the present invention are absorbed in warm-blooded animals, they switch on the signals at their respective receptors to cause their pharmacological actions. Hence, even when their plasma concen-trations decrease below the threshold plasma levels to cause each drug's effects, the switches located at their receptors have already been turned on and so the preventative or therapeutic effects on hypertension caused by the first drug are seen. The effects of the compound that is administered later are superimposed on those of the former drug. Thus the actions of these 2 agents are additive and excellent effects can be observed. Since it is clinically convenient if these 2 agents are administered at the same time, the specific angiotensin II receptor antagonist, such as CS-866, and the diuretics can be administered at the same time as a single pharmaceutical composition. In the case that these agents cannot adequately be mixed physically from formulation techniques, each compound may be separately administered at the same time. Furthermore, as described above, since these 2 groups of agents do not necessarily have to be administered at the same time to get excellent therapeutic efficacy, the compounds may be administered at appropriate intervals. The maximum acceptable time interval to administer these 2 groups of compounds to obtain excellent treatment or preventative efficacy can be confirmed clinically or preclinically.

The administration route of specific angiotensin II receptor antagonists, such as CS-866, and diuretics is generally oral. Thus these 2 groups of compounds can be prepared as separate single formulations of each or as a single formulation by physically mixing these 2 groups of compounds. Administration formulations are, for instance, powder, granules, tablets, capsules, etc. The free compounds or pharmacologically acceptable salts or esters thereof are mixed with constituents, diluents, etc., and prepared according to conventional preparation techniques as described below.

Namely, preparations as described above are manufactured by conventionally known methods using additive agents, i.e., carriers such as diluents (for instance, organic diluents including sugar derivatives such as lactose, sucrose, glucose, mannitol, sorbitol; starch derivatives such as cornstarch, potatostarch, α-starch, and dextrin; cellulose derivatives such as crystalline cellulose; gum arabic; dextran; pullulan; and inorganic diluents including silicate derivatives such as light anhydrous silicic acid, synthetic aluminum silicate, calcium silicate, magnesium aluminometasilicate; phosphate derivatives such as calcium hydrogenphosphate; carbonates such as calcium carbonate; and sulfate derivatives such as calcium sulfate), lubricants (for instance, metallic salts of stearic acid such as stearic acid, calcium stearate, magnesium stearate; talc; waxes such as beeswax, spermaceti; boric acid; adipic acid; sulfates such as sodium sulfate; glycol; fumaric acid; sodium benzoate; DL-leucine; laurylsulphates such as sodium lauryl sulfate, magnesium lauryl sulfate; silicates such as anhydrous silicic acid, silicic acid hydrates; and starch derivatives described above can be listed), binders (for instance, hydroxypropylcellulose, hydroxypropylmethylcellulose, polyvinylpyrrolidone, macrogol, and similar diluents described above), disintegrators (for instance, cellulose derivatives such as low-substituted hydroxypropylcellulose, carboxymethylcellulose, sodium carboxymethylcellulose, and internally bridged-sodium carboxymethylcellulose; chemically modified starch/cellulose derivatives such as carboxymethylstarch, sodium carboxymethylstarch, bridged polyvinylpyrrolidone; and starch derivatives described above), demulsifiers (for instance, colloidal clay such as bentonite and veegum; metal hydrates such as magnesium hydroxide, aluminum hydroxide; anionic surfactants such as sodium lauryl sulfate, calcium stearate; cationic surfactants such as benzalkonium chloride; and non-ionic surfactants such as polyoxyethylenealkyl ether, and polyoxyethylene sorbitan fatty acid ester, and sucrose esters fatty acids), stabilizers (for instance, parahydroxybenzoates such as methylparaben and propylparaben; alcohols such as chlorobutanol, benzylalcohol, phenylethylalcohol; benzalkonium chloride; phenols such as phenol and cresol; thimerosal; dehydroacetic acid; and sorbic acid), flavors (for instance, sweeteners, acidifiers, and conventionally used flavors), etc.

The dose and rate of administration of the specific angiotensin II receptor antagonist, such as CS-866, and diuretics depend upon various factors such as the drugs' activities, symptoms, age, and body weight of the patients. However, generally speaking, the adult dosage (mg dose/time) of the specific angiotensin II receptor antagonist and diuretics is 0.5 to 1,000 mg (preferably 1 to 100 mg) and about 0.05 to 1,500 mg (preferably 5 to 300 mg), respectively. Compounds are administered once or several times per day, depending upon the symptoms of the patients.

Dosing ratios of the drugs in the 2 categories may also be varied. However, generally speaking, the rates of the specific angiotensin II receptor antagonist, such as CS-866, and diuretics are 1:200 to 200:1 as their weight ratios.

In the present invention, the specific angiotensin II receptor antagonist, such as CS-866, and diuretics are simultaneously administered, or separately or sequentially administered at the doses described above.

The present invention is described in more detail by way of the following Examples. However, the present invention is not limited to these examples.

TEST EXAMPLE 1
Hypotensive Effects Elicited by Co-Administration of CS-866 and Hydrochlorothiazide Twenty-eight male spontaneously hypertensive rats aged 20 weeks (SHRs, SPF grade, purchased from Hoshino Laboratory Animals) were used. A transmitter of a telemeter (TA11PA-C40, DATA SCIENCES Inc.) was implanted in each SHR for recording blood pressure. After recovery from the surgical operations, blood pressure was monitored in the rats from the age of 24 weeks. The rats were orally given 0.5% carboxymethylcellulose solution (CMC, 2 ml/kg) for 7 successive days (once daily) by gavage. They were divided into 4 groups (7 SHRs per group) so as to give equally averaged blood pressure levels in the groups based on the blood pressure recorded on the 5th and 6th days after the CMC solution was initiated. The rats were orally treated with 0.5% CMC solution (2 ml/kg, control group) or test substance suspended in 0.5% CMC solution (2 ml/kg) for 14 successive days (once daily). Blood pressure was monitored 1 day prior to the drug administration and on the 7th and 14th days after the drug was initiated. The group composition, test substances, doses and blood pressure (the 24 hour mean blood pressure±standard error on the respective monitoring days) are summarized in Tables 1 and 2.

The test substances were hydrochlorothiazide (HCTZ), CS-866, and HCTZ and CS-866.HCTZ was prepared so as to be 10 mg/2 ml of final concentration with 0.5% CMC solution. CS-866 was suspended in 0.5% CMC solution so as to be at a final concentration of 1 mg/2 ml. CS-866 and HCTZ solution was prepared so as to be at a final concentration of [10 mg (HCTZ)+1 mg (CS-866)]/2 ml with 0.5% CMC solution.

TABLE 1

Group composition and administration of the test substance

| Group 1 | Control | 0.5% CMC solution |
| Group 2 | HCTZ | HCTZ (10 mg/kg) |
| Group 3 | CS-866 | CS-866 (1 mg/kg) |
| Group 4 | HCTZ and CS-866 | HCTZ (10 mg/kg) + CS-866 (1 mg/kg) |

TABLE 2

Blood pressure levels

| | Group 1 | Group 2 | Group 3 | Group 4 |
|---|---|---|---|---|
| 1 day before administration | 167 ± 6 | 165 ± 6 | 167 ± 6 | 165 ± 4 |
| 7th day after administration | 163 ± 6 | 152 ± 6 | 147 ± 4 | 132 ± 4 |
| 14th day after administration | 166 ± 7 | 156 ± 6 | 148 ± 4 | 134 ± 4 |

As summarized in Table 2, co-administration of CS-866 and HCTZ (Group 4) showed a more excellent hypotensive action than those elicited by each of the agents CS-866 and HCTZ alone (Group 2 or 3).

Preparation Example 1

Tablets

| CS-866 | 10.0 mg |
| Hydrochlorothiazide | 12.5 mg |
| Lactose | 275.5 mg |
| Cornstarch | 50.0 mg |
| Magnesium stearate | 2.0 mg |
| Total | 350 mg |

The powders described above are mixed well, and tableted with a tableting machine to prepare a tablet containing 350 mg. The tablets can be sugar coated if desired.

What is claimed is:

1. A method for treating hypertension comprising administering to a warm-blooded animal in need thereof a pharmaceutically effective amount of each of (i) an angiotensin II receptor antagonist selected from the group consisting of a compound having the following formula (I):

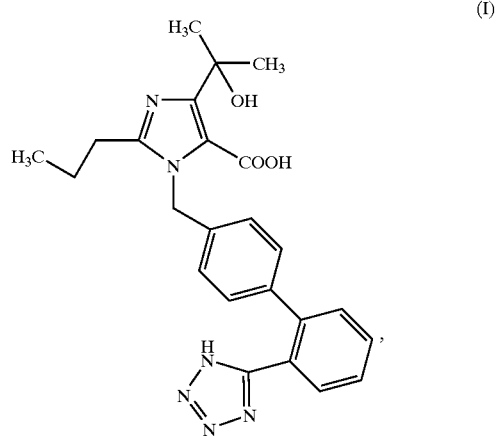

a pharmacologically acceptable salt thereof, a pharmacologically acceptable ester thereof and a pharmacologically acceptable salt of said ester thereof, and (ii) a diuretic which is hydrochlorothiazide.

2. The method according to claim 1, wherein the warm-blooded animal is a human.

3. The method according to claim 2, wherein the angiotensin II receptor antagonist is the compound of the formula (I) or a pharmacologically acceptable ester hereof.

4. The method according to claim 2, wherein the angiotensin II receptor antagonist is a pharmacologically acceptable ester of the compound of the formula (I).

5. The method according to claim 2, wherein the angiotensin II receptor antagonist is the pivaloyloxymethyl ester, phthalidyl ester, or (5-methyl-2-oxo-1,3-dioxolen-4-yl) methyl ester of the compound of the formula (I).

6. The method according to claim 2, wherein the angiotensin II receptor antagonist is the (5-methyl-2-oxo-1,3-dioxolen-4-yl)methyl ester of the compound of th formula (I).

7. The method according to claim 2, wherein the diuretic further comprises one or more diuretics selected from the group consisting of methylclothiazide, benzylhydrochlorothiazide, trichlormethiazide, cyclopenthiazide, polythiazide, ethiazide, cyclothiazide, bendroflumethiazide and hydroflumethiazide.

8. The method according to claim 2, wherein a weight ratio of amounts of the compound of the formula (I) to the diuretic is 1:200 to 200:1.

9. The method according to claim 3, wherein a weight ratio of amounts of the compound of the formula (I) to the diuretic is 1:200 to 200:1.

10. The method according to claim 5, wherein a weight ratio of amounts of the compound of the formula (I) to the diuretic is 1:200 to 200:1.

11. The method according to claim 2, wherein the compound of the formula (I) is administered at least once a day in an amount of 0.5 to 1,000 mg and the diuretic is administered at least once a day in an amount of 0.05 to 1,500 mg.

12. The method according to claim 2, wherein the compound of the formula (I) is administered at least once a day in an amount of 1 to 100 mg and the diuretic is administered at least once a day in an amount of 5 to 300 mg.

13. The method according to claim 6, wherein a weight ratio of amounts of the compound of the formula (I) to the diuretic is 1:200 to 200:1.

14. The method according to claim 6, wherein the compound of the formula (I) is administered at least once a day in an amount of 0.5 to 1,000 mg and the diuretic is administered at least once a day in an amount of 0.05 to 1,500 mg.

15. The method according to claim 6, wherein the compound of the formula (I) is administered at least once a day in an amount of 1 to 100 mg and the diuretic is administered at least once a day in an amount of 5 to 300 mg.

* * * * *